United States Patent
Yanagida (10) Patent No.: US 9,687,201 B2
(45) Date of Patent: Jun. 27, 2017

(54) X-RAY CT SYSTEM

(75) Inventor: Yuuji Yanagida, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 222 days.

(21) Appl. No.: 13/995,350

(22) PCT Filed: Apr. 12, 2012

(86) PCT No.: PCT/JP2012/060080
§ 371 (c)(1),
(2), (4) Date: Jun. 18, 2013

(87) PCT Pub. No.: WO2012/144427
PCT Pub. Date: Oct. 26, 2012

(65) Prior Publication Data
US 2013/0279644 A1 Oct. 24, 2013

(30) Foreign Application Priority Data
Apr. 20, 2011 (JP) ................. 2011-094149

(51) Int. Cl.
*A61B 6/03* (2006.01)
*A61B 6/10* (2006.01)
*A61B 6/00* (2006.01)

(52) U.S. Cl.
CPC ............. *A61B 6/032* (2013.01); *A61B 6/10* (2013.01); *A61B 6/544* (2013.01)

(58) Field of Classification Search
CPC ........... A61B 6/12; A61B 6/032; A61B 6/541; A61B 6/542
See application file for complete search history.

(56) References Cited

U.S. PATENT DOCUMENTS 6,954,513 B2* 10/2005 Horiuchi ............... A61B 6/583
378/165
7,190,763 B2  3/2007 Mungilwar
(Continued)

FOREIGN PATENT DOCUMENTS

JP  2004 195121  7/2004
JP  2005 185648  7/2005
(Continued)

OTHER PUBLICATIONS

International Search Report Issued May 15, 2012 in PCT/JP12/060080 Filed Apr. 12, 2012.

*Primary Examiner* — Hoon Song
(74) *Attorney, Agent, or Firm* — Oblon, McClelland, Maier & Neustadt, L.L.P.

(57) ABSTRACT

An X-ray CT system is provided that determines input imaging conditions based on the attributes of subjects that were measured by the apparatus itself and can prevent excessive radiation exposure due to human error. The X-ray CT system comprises a measurement unit, a part identification unit, a calculation unit, a comparison unit, and a notification unit. The measurement unit measures the attributes of a subject placed on a couch. The part identification unit identifies the part of the subject being imaged based on the measured attributes of the subject. The calculation unit calculates a radiation dose based on the identified unit being imaged. The comparison unit makes a determination by comparing the calculated radiation dose and the radiation dose based on the imaging conditions input for examination. The notification unit notifies the results determined by the comparison unit.

14 Claims, 5 Drawing Sheets

(56) References Cited

U.S. PATENT DOCUMENTS

| | | | |
|---|---|---|---|
| 8,189,740 B2 | 5/2012 | Tsukagoshi et al. | |
| 2007/0081630 A1* | 4/2007 | Evron | A61B 5/02007 378/108 |
| 2009/0074143 A1* | 3/2009 | Tsukagoshi et al. | 378/97 |
| 2010/0014630 A1* | 1/2010 | Goto | A61B 5/4869 378/16 |

FOREIGN PATENT DOCUMENTS

| | | |
|---|---|---|
| JP | 2005 270286 | 10/2005 |
| JP | 2009 66288 | 4/2009 |
| JP | 2011 45709 | 3/2011 |

* cited by examiner

| THE PART BEING IMAGED ADULTS · CHILDREN | THE IMAGING CONDITIONS | | | MEDICAL INSTITUTION THE RADIATION DOSE (mGy) |
|---|---|---|---|---|
| | THE TUBE VOLTAGE (kV) | TUBE CURRENT (mA) | EXPOSURE TIME (sec) | |
| THE CHEST/ADULTS (AP) | ... | ... | ... | ... |
| (Lat) | ... | ... | ... | ... |
| THE CHEST/ADULTS (PORTABLE) | ... | ... | | ... |
| THE CHEST/CHILDREN (SIX YEARS OLD) | ... | ... | ... | ... |
| THE CHEST/INFANTS (SIX MONTHS OLD) | ... | ... | ... | ... |

FIG. 5

X-RAY CT SYSTEM

TECHNICAL FIELD

The present invention relates to an X-ray CT system that reconstructs tomogram images of a subject based on X-rays transmitting the subject.

BACKGROUND ART

Acceptable radiation doses may differ according to the part to be imaged depending on the development risk of cancer and their hereditary impact in tissues exposed to radiation during X-ray imaging.

The effective dose (Sv) indicating the acceptable radiation dose is represented by the following formula.

Effective dose=total amount Σ all tissues (tissue weighting factor×equivalent dose)

Here, the tissue weighting factor is a numerical value representing relatively the absorbed dose (Gy) which received in each tissue. Tissue weighting factors in the 2007 recommendations by the International Commission on Radiological Protection (ICRP) include 0.12 for the breasts, bone marrow (red), colon, and lungs; 0.08 for the stomach, gonads; 0.04 for the thyroid gland, esophagus, liver, and bladder; 0.01 for the bone surface, skin, brain, and salivary glands; and 0.12 for the remaining tissues and organs. The effective dose becomes 1.00 when these tissue weighting factors are multiplied by each equivalent dose and summed up. With regard to the tissue weighting factor, tissues with larger factors have a higher development risk of cancer, etc. than tissues with smaller factors even with the same equivalent dose. Furthermore, the equivalent dose is a value calculated by multiplying the absorbed dose and the radiation weighting factor. The radiation weighting factor differs according to the kind of radiation. For example, the radiation weighting factor of X-rays is "1."

As mentioned above, the acceptable radiation dose is set according to the part being imaged (tissues and organs included).

Based on the said ICRP recommendations, health related administrative agencies (such as the Ministry of Health, Labor and Welfare) and health related organizations (such as medical associations in each country) officially define standard doses in terms of the part being imaged, adults, children, sex, physique, laboratory procedure, etc.

Figure 4:
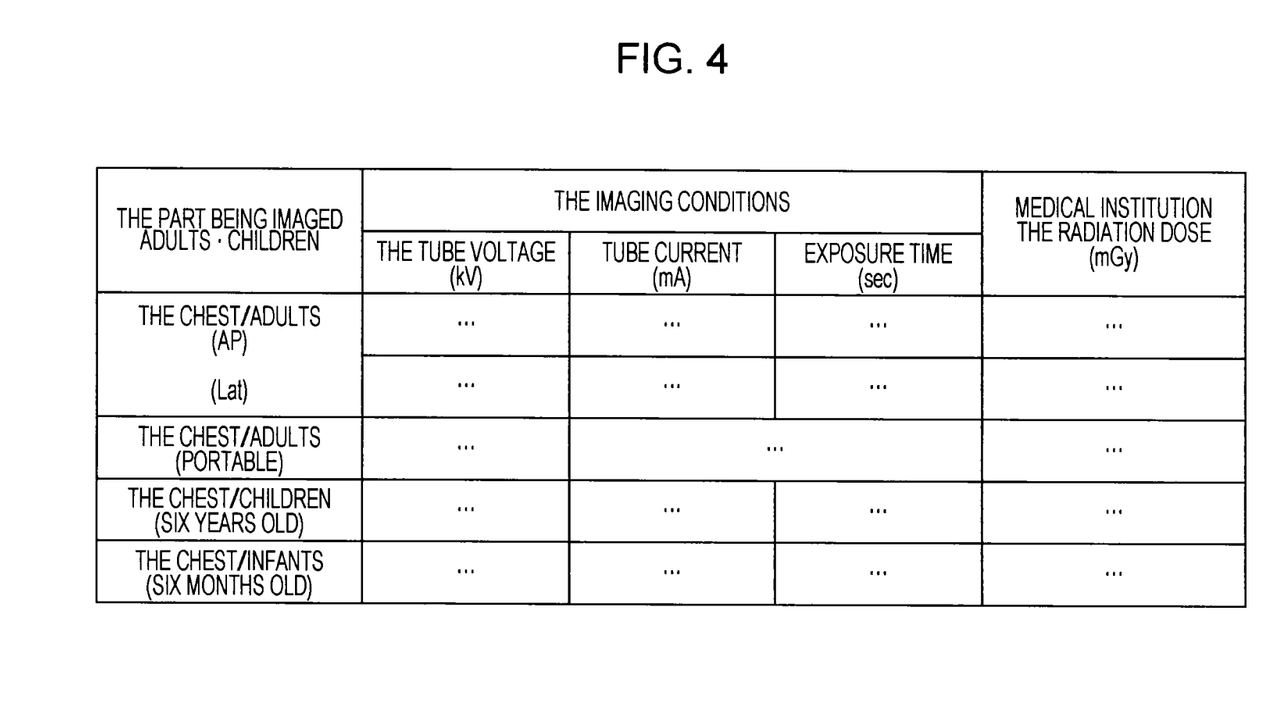
FIG. 4 is a table indicating an example of the correlation between the part being imaged as well as the subject's attributes and standard dose.

Health care professionals (such as radiologists) at each medical institution register a standard dose in the X-ray CT system in advance. FIG. 4 is a table showing an example of standard doses for the chest that is selected as a part to be imaged. Incident surface doses (mGy) are specified for each part to be imaged (chest) and subject attribute (adults, children, and infants) in the standard doses illustrated in FIG. 4.

X-ray CT system users at each medical institution such as medical technologists (hereinafter, referred to as technologists) input the imaging conditions including the tube voltage, tube current, exposure time, part to be imaged, filming range, and filming technique (such as taking multiple images of the same position) in addition to subject (patient) attributes such as age, sex, and weight (physique) before performing an X-ray imaging.

Technologists may input incorrect imaging conditions (human error). Measures to prevent this from happening have been established.

If the radiation dose based on the imaging conditions input by technologists is determined to be inappropriate for medical radiation exposure, systems using conventional technology will alert of inappropriate imaging conditions.

This technology can prevent excessive exposure to radiation by alerting of inappropriate imaging conditions and allowing technologists to correct the imaging conditions if imaging conditions such as the tube voltage and tube current are input incorrectly due to factors such as lack of knowledge and insufficient attention by the technologists.

Systems using conventional technology will alert of inappropriate radiation doses based on the patient information that is input prior to performing an X-ray imaging because the acceptable radiation dose differs depending on subject attributes such as physique, sex, and age.

Figure 5:
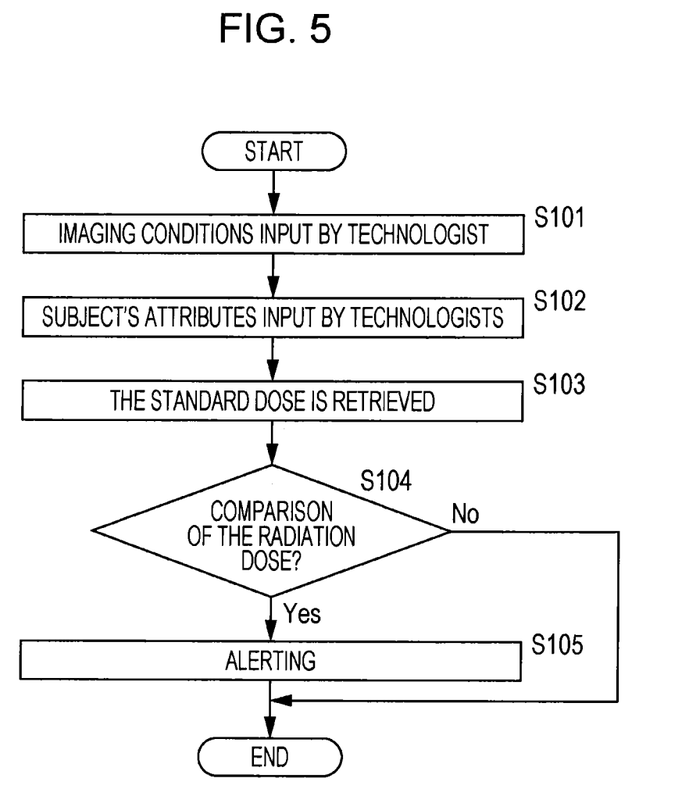
FIG. 5 is a flow chart indicating a series of processes from inputting imaging conditions to alerting.

FIG. 5 is a flow chart indicating a series of processes from inputting imaging conditions to alerting. As shown in FIG. 5, imaging conditions are input by technologists prior to taking an X-ray image (step S101). Then, the subject's attributes are input by technologists (step S102). After that, the standard dose is retrieved (step S103). Next, the X-ray CT system determines whether the radiation dose is appropriate or not by comparing the radiation dose that is calculated based on imaging conditions input by technologists and the subject's attributes to the standard dose (step S104). Then, the system will alert that the imaging conditions are inappropriate (step S105) if, for example, the radiation dose is an excessive radiation dose that is over the reference dose (step S104: Yes).

Furthermore, as an example of a general method for calculating radiation dose based on the imaging conditions, one method calculates the radiation dose based on the part being imaged as well as the tube voltage, tube current, detector mode, helical pitch, and filming range of the X-ray tubes. There is also a method that calculates the radiation dose based on the tube voltage of the X-ray tubes, blade position of the collimator, exposed area, tube current, and X-ray exposure time (for example, Patent Document 1).

PRIOR ART DOCUMENTS

Patent Documents

[Patent Document 1] Japanese published unexamined application No. 2005-185648

SUMMARY OF THE INVENTION

Problems to be Resolved by the Invention

There was a problem in that excessive exposure to radiation may occur with these conventional technologies; however, because they may not alert to prevent excess exposure to radiation when appropriate imaging conditions are not input (human error) due to factors such as lack of knowledge and insufficient attention by the technologist as well as if there is no opportunity to correct the imaging conditions.

This embodiment is for solving said problem with the intention of providing an X-ray CT system that can prevent excessive radiation exposure caused by human error by determining whether or not input imaging conditions are appropriate based on patient attributes measured by the apparatus itself.

Means of Solving the Problems

In order to solve said problem, the X-ray CT system in the embodiment comprises a measurement unit, part identification unit, calculation unit, comparison unit, and notification unit. The measurement unit measures the attributes of a subject placed on a couch. The part identification unit specifies the part of the subject to be imaged based on the measured attributes of the subject. The calculation unit calculates the radiation dose based on specified imaging part. The comparison unit makes a judgment by comparing the calculated radiation dose to the radiation dose based on the imaging conditions input during an examination. The notification unit notifies results determined by the comparison unit.

MODE FOR CARRYING OUT THE INVENTION

The embodiment of the X-ray CT system will be explained with reference to each figure.

Figure 1:
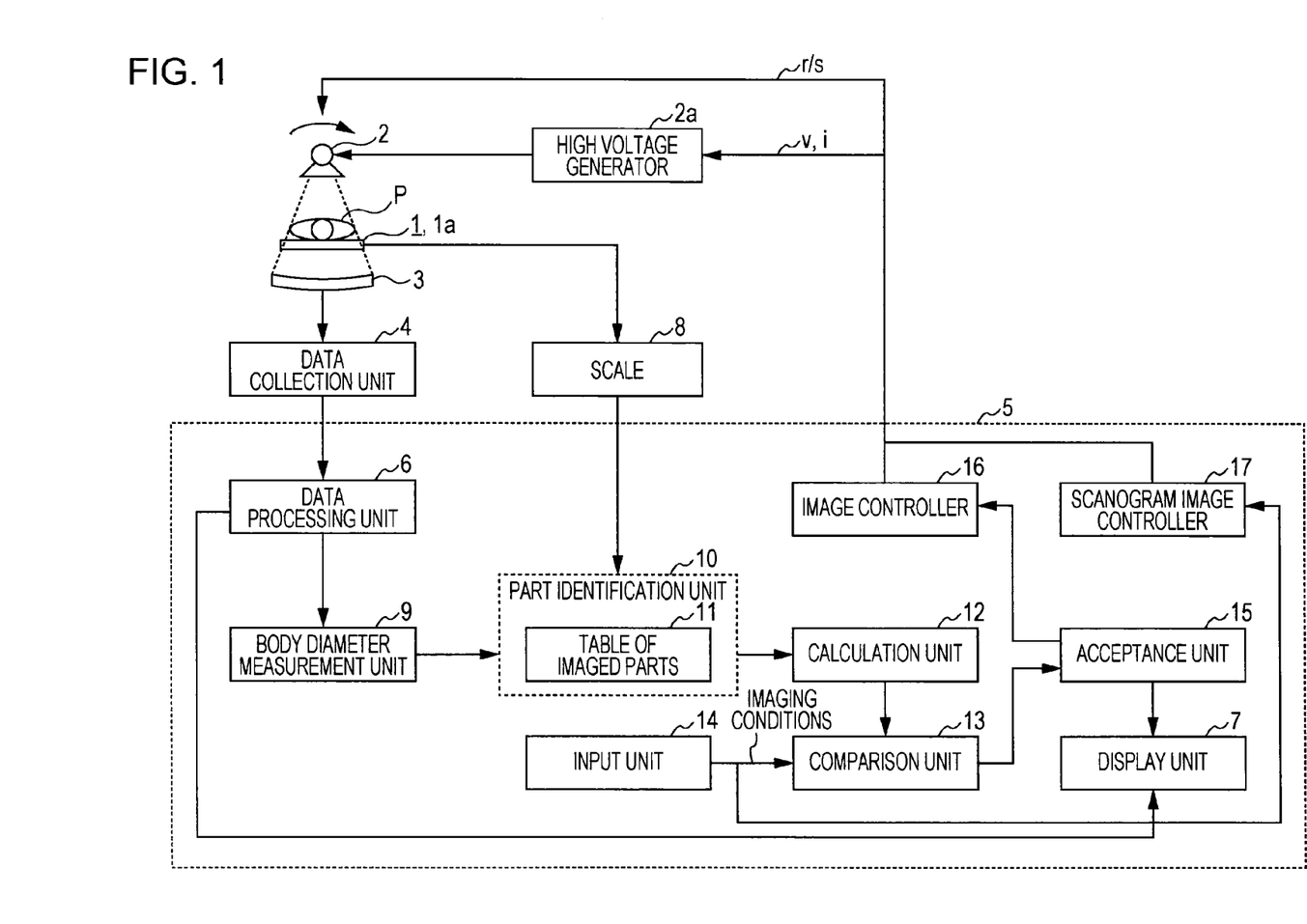
FIG. 1 is a block diagram indicating the composition of the X-ray CT system related to one embodiment.

FIG. 1 is a block diagram indicating the composition of the X-ray CT system. As FIG. 1 indicates, the X-ray CT system comprises a couch 1, X-ray tubes 2, an X-ray detector 3, a data collection unit 4, and a console 5. The console 5 comprises a data processing unit 6 and a display unit 7.

The couch 1 comprises a couch top 1a on which the subject P is placed, a couch top driving means (illustration omitted) that enables adjustment of the imaging position by moving the couch top 1a towards the body axis of the subject and a helical scan, and a scale 8.

The X-ray tubes 2 and X-ray detector 3 are provided in a rotor (illustration omitted) such that they are placed facing each other with the couch top 1a on which subject P is placed between them. A high voltage generator 2a applies high voltage to the X-ray tubes 2 by receiving control information (described later) from the console 5. The X-ray tubes 2 irradiate the X-ray fan beam that has energy corresponding to the tube voltage, tube current, etc. towards the subject P. The X-ray detector 3 is composed of an X-ray detecting element array on which multiple X-ray detecting elements (illustration omitted) are placed two-dimensionally in both the rotating direction and the body axis direction.

The data collection unit 4 retrieves detection signals of the X-ray that transmits the subject P and converts it into digital data to send the data to the data processing unit 6.

The data processing unit 6 comprises a preprocessing part that generates projection data by performing various processes on digital data that is sent from the data collection unit 4, a reconfiguration process part that generates image data that becomes a tomographic image of the subject P by performing reconfiguration processing on the projection data, a memory part that stores generated image data, and an image processing part that converts to various image data based on the image data.

The display unit 7 retrieves tomographic image data that is generated by the image processing part and displays the tomographic image on the display screen of a monitor (illustration omitted).

Tomographic images of the subject P can be acquired based on the X-ray irradiated by X-ray tubes 2 and transmitted to the subject P according to said composition of the X-ray CT system (real scan).

A prescan is performed prior to the real scan in order to perform alignment of the subject P and configuration of the filming range. As an example of prescanning, a front fluoroscopic image and side fluoroscopic image are acquired by transmitting the front and side of the subject P using X-rays. The acquired front fluoroscopic image and side fluoroscopic image are stored in the memory part of the data processing unit 6. The front fluoroscopic image and side fluoroscopic image are sometimes called scanograms.

As an example of the means to measure the weight of the subject P placed on the couch top 1a, technology that is listed in unexamined patent application publication 2010-17457 should be used. That is, the weight of the subject P is calculated from the load difference between the load with the subject P placed on the couch top 1a and the load without the subject P on the couch top 1a, which are measured using the scale 8 that is provided on the couch 1.

The console 5 comprises a body diameter measurement unit 9, a part identification unit 10, a table of imaged parts 11, a calculation unit 12, a comparison unit 13, an input unit 14, an acceptance unit 15, an image controller 16, and a scanogram image controller 17.

The body diameter measurement unit 9 measures the body diameter of the front side of the subject P based on a front fluoroscopic image that is retrieved from the memory part of the data processing unit 6.

The part identification unit 10 identifies the part being imaged by receiving the weight of the subject P measured by the scale 8 and the body diameter of the subject P measured by the body diameter measurement unit 9, then referencing the table of imaged parts 11.

Figure 2:
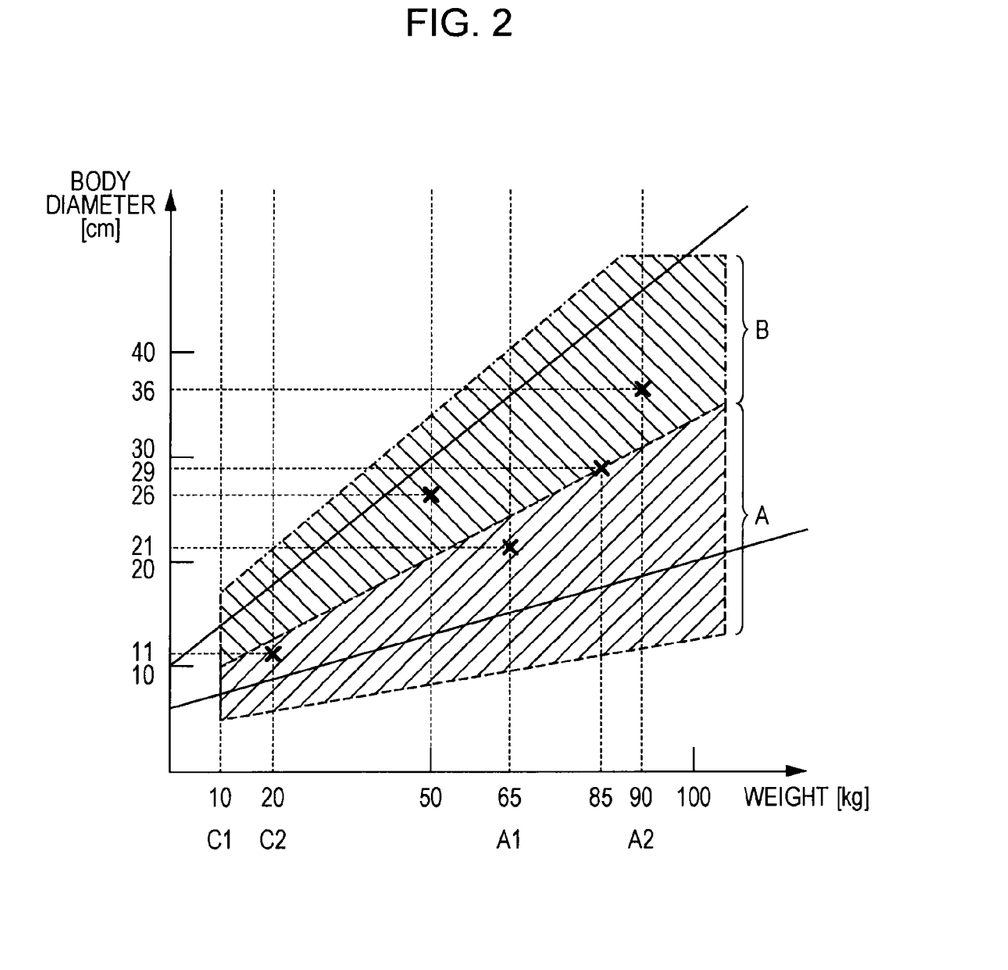
FIG. 2 is a diagram indicating the correlation between weight and body diameter of a subject and the part to be imaged.

FIG. 2 is a figure indicating the correlation between weight and the body diameter of the subject P and the part being imaged using the weight of the subject P as the abscissa and the body diameter of the subject P as ordinate. The region equivalent to the head and the region equivalent to the thoracoabdominal part, which are divided by a boundary line, are indicated as "A" and "B" in FIG. 2. Subjects P weighing 10, 20, 65, and 90 [kg] are considered to be an "infant," "child," "standard adult," and "obese adult" and indicated as "C1," "C2," "A1," and "A2" in FIG. 2.

How the part identification unit 10 specifies a part being imaged is explained with reference to FIG. 2. For example, if the subject P weighs 20 [kg] and has body diameter 11, the region equivalent to the head is specified. Similarly, if the subject P weighs 50 [kg] and has body diameter 26, the region equivalent to thoracoabdominal part is specified. Furthermore, if the subject P weighs 65 [kg] and has body diameter 21, the region equivalent to the head is specified. Subsequently, if the subject P weighs 90 [kg] and has body diameter 36, the region equivalent to thoracoabdominal part is specified.

As stated above, if the weight and body diameter of the subject P are not near the boundary between the region equivalent to the head A and the region equivalent to the thoracoabdominal part B, the part identification unit 10 may specify either the region equivalent to the head or the region equivalent to the thoracoabdominal part. For example, if the subject P's weight and body diameter are in the vicinity of the boundary between the region equivalent to the head A and the region equivalent to the thoracoabdominal part B such that the subject P weighs 85 [kg] and has body diameter 29, the part identification unit 10 does not specify either the region equivalent to the head or the region equivalent to the thoracoabdominal part. That is, the part identification unit 10 outputs a signal indicating that it does not specify either the region equivalent to head or the region equivalent to thoracoabdominal part. The display unit 7 notifies an alarm after receiving the signal. The area of the vicinity range of the boundary may be adjusted.

The calculation unit 12 calculates the radiation dose based on the specified part being imaged by the part identification unit 10. For example, a table corresponding to the part being imaged and the radiation dose indicated in FIG. 4 should be referred.

In contrast, the radiation dose is calculated by said general method based on the imaging conditions configured by technologists using the input unit 14.

The comparison unit 13 compares the radiation dose that is calculated by the calculation unit 12 based on the specified part being imaged to the radiation dose based on the imaging conditions configured by the technologist using the input unit 14 and outputs the results regarding whether or not the imaging conditions are appropriate.

The acceptance unit 15 outputs the imaging conditions input by operation of the input unit 14 to the image controller 16 when the imaging conditions are determined to be appropriate by the comparison unit 13. The acceptance unit 15 outputs the results to the display unit 7 if the imaging conditions are determined to be inappropriate by the comparison unit 13. The display unit 7 then notifies the results indicating that the imaging conditions are inappropriate. The display unit 7 is equivalent to an example of a "notification unit." The results from the comparison unit 13 may also be displayed on the display unit 7 regardless of the propriety of the imaging conditions.

The image controller 16 generates control information based on the imaging conditions (imaging conditions input by the operation of the input unit 14) output by the acceptance unit 15 and outputs the information to a high voltage generator 2a, the rotor driving means (illustration omitted) that rotates and a rotor with a specified rotating speed (r/s), and the couch top driving means (illustration omitted), etc. This allows a real scan to be performed based on the information.

Figure 3:
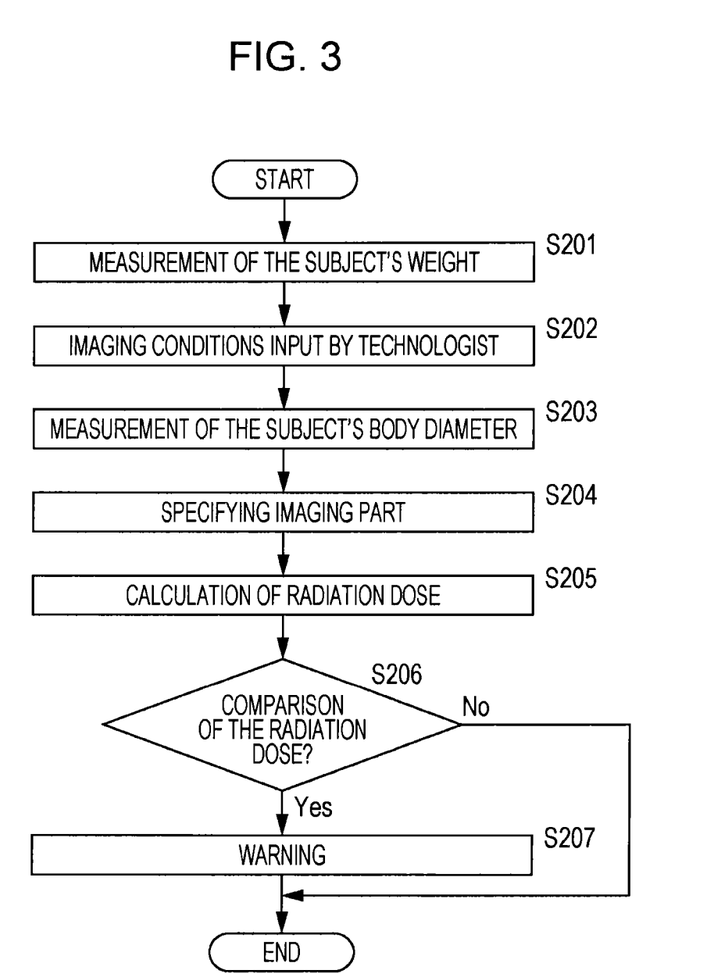
FIG. 3 is a flow chart indicating a series of processes from inputting imaging conditions to alerting.

The scanogram image controller 17 generates control information based on imaging conditions input by the operation of the input unit 14 and outputs the information to the high voltage generator 2a, the rotor driving unit, and the couch top driving unit, etc. This allows a prescan to be performed based on the information The process that determines the propriety of the radiation dose based on measured results after measuring the attributes of the subject P is explained next with reference to FIG. 3. FIG. 3 is a flow chart that indicates a series of processes from inputting imaging conditions to alerting.

(Step S201: Measurement of the Subject's Weight)

First, a technologist places the subject (patient) P who is brought into the laboratory on the couch top 1a of the couch 1 and moves the couch top 1a to an appropriate position for X-ray imaging.

The scale 8 embedded in the couch 1 measures the weight of the subject P placed on the couch top 1a at this time. The measured weight of the subject P is stored in a memory part (illustration omitted) as a piece of attribute information of the subject P.

(Step S202: Imaging Conditions Input)

Subsequently, the technologist goes to an operation room where the console 5 is provided and inputs imaging conditions using the input unit 14. The input imaging conditions are stored in the memory part (illustration omitted).

(Step S203: Measurement of the Subject's Body Diameter)

After the technologist inputs the imaging conditions, a scanogram is taken in preparation for correctly specifying a range in which an X-ray CT will be performed. The scanogram takes a front fluoroscopic image and a side fluoroscopic image of the subject P from one direction (front and side) on the couch top; however, the range including parts where the tomographic image should be acquired is actually taken in order to specify a range in which a tomographic image of the subject P is acquired accurately. The body diameter measurement unit 9 automatically calculates the body diameter of the subject P inside the scanogram by identifying the patient and space based on the acquired pixel value of the scanogram.

(Step S204: Specifying Imaging Part)

The part identification unit 10 specifies whether the part of the subject P being imaged as the region equivalent to the head or the region equivalent to thoracoabdominal part based on subject P's weight measured by the scale 8 in advance and subject P's body diameter measured by the body diameter measurement unit 9 with reference to the table of imaged parts 11 that is contained internally.

(Step S205: Calculation of Radiation Dose)

The calculation unit 12 calculates the radiation dose based on the specified part being imaged.

As an example of radiation dose, the effective dose indicated in said ICRP recommendations may be used, the numerical value calculated by said general method based on each value of the imaging conditions may also be used, or the standard dose based on the table indicated in FIG. 4 may also be used.

(Step S206: Comparison of the Radiation Dose)

The comparison unit 13 compares the radiation dose based on the imaging conditions input by a technologist in step S202 to the radiation dose calculated based on the specified part being imaged that is calculated in step S205.

The comparison unit 13 determines whether or not the input imaging conditions are appropriate by comparing the radiation doses.

With regard to comparison of the radiation dose, for example, the comparison unit 13 determines whether or not the radiation dose based on the input imaging conditions is excessive against the part being imaged by comparing radiation doses.

An example of the determination as to whether or not the radiation dose based on the input imaging conditions is excessive will be explained here. If the radiation dose based on the input imaging conditions is Di [mGy] and the radiation dose that is the basis of comparison (permissible value) is Da [mGy], the comparison unit 13 determines the input imaging conditions to be "true" when Di≤Da and the comparison unit 13 determines the input imaging conditions to be "error" when Di>Da.

(Step S207: Warning)

If the comparison unit 13 determines the input imaging conditions are inappropriate (step S206: Yes), a comparison result is output from the comparison unit 13 to the acceptance unit 15 and the comparison result is output from the acceptance unit 15 to the display unit 7. The display unit 7 then displays an alarm on its display screen to alert the error input of the imaging conditions (human error). The imaging conditions are not output from the acceptance unit 15 to the image controller 16. As a result, X-ray imaging based on inappropriate imaging conditions will not be performed and excessive exposure to radiation can be prevented.

The technologist looks at the displayed alarm and checks imaging conditions that were entered incorrectly and re-enters the imaging conditions (step S202). As long as the comparison unit 13 determines that the re-entered imaging conditions are inappropriate (step S206: Yes), the acceptance unit 15 outputs the comparison results to the display unit 7 and the display unit 7 displays an alarm (step S207). Furthermore, the acceptance unit 15 does not output the imaging conditions to the image controller 16 so that X-ray imaging based on inappropriate imaging conditions is prevented. If the technologist decides to perform X-ray imaging based on these imaging conditions, for example, by satisfying conditions such as entering a password, X-ray imaging is permitted and the acceptance unit 15 outputs the imaging conditions to the image controller 16.

In contrast, if the comparison unit 13 determines the input imaging conditions are inappropriate (step S206: No), the acceptance unit 15 outputs the imaging conditions to the image controller 16 after receiving the decision results.

If the comparison unit 13 determines that the re-entered imaging conditions are inappropriate after the alarm is displayed in step S207 (step S206: No), the acceptance unit 15 outputs the imaging conditions to the image controller 16 for the first time.

The image controller 16, therefore, generates control information based on the imaging conditions and outputs the control information to the high voltage generator 2a, the rotor driving means (illustration omitted), and the couch top driving means (illustration omitted). The high voltage generator 2a applies high voltage based on the imaging conditions to the X-ray tubes 2 and the rotor driving means rotates the X-ray tubes 2 and the X-ray detector 3 around the subject P. The couch top driving means moves the couch top 1a. The X-ray detector 3 is projected from the X-ray tubes 2 and detects X-rays that were transmitted through the subject P. A tomographic image of the subject P is acquired by performing reconfiguration processing on projection data based on X-ray detection signals. X-ray imaging based on appropriate imaging conditions, therefore, is performed.

Some embodiments of this invention were explained but these embodiments are presented as examples and are not intended to limit the scope of the invention. These new embodiments may be performed in other various forms and various omissions, revisions, and changes can be made as long as there is no deviation from the fundamentals of the invention. These embodiments and their variations are included in the scope and fundamentals of the invention as well as in the inventions listed in the scope of patent claims and their equivalent scope.

DESCRIPTION OF SYMBOLS

1 Couch
1a Couch top
2 X-ray tubes
2a High voltage generator
3 X-ray detector
4 Data collection unit
5 Console
6 Data processing unit
7 Display unit
8 Scale
9 Body diameter measurement unit
10 Part identification unit
11 Table of imaged parts
12 Calculation unit
13 Comparison unit
14 Input unit
15 Acceptance unit
16 Image controller
17 Scanogram image controller
16 Image controller

The invention claimed is:

1. An X-ray CT system, wherein;
a tomographic image of a subject is captured based on X-rays that are projected from an X-ray tube towards a subject placed on a couch and that transmit the subject, further comprising:
a part identification unit that identifies the part of the subject being imaged based on weight and body diameter of the subject placed on the couch;
a calculation unit that acquires the radiation dose based on an identified unit being imaged;
a comparison unit that makes a determination by comparing the acquired radiation dose and radiation dose based on imaging conditions that are input for examination; and
a notification unit that notifies the results determined by the comparison unit.

2. An X-ray CT system, wherein;
a tomographic image of a subject is captured based on X-rays that are projected from an X-ray tube towards a subject placed on a couch and that transmit the subject, further comprising:
an input unit for inputting imaging conditions for capturing the subject;
an image control unit that generates control information based on the input imaging conditions;
a part identification unit that identifies a unit of the subject being imaged based on weight and body diameter of the subject placed on the couch;
a calculation unit that acquires the radiation dose based on an identified part being imaged;
a comparison unit that determines whether the input imaging conditions are appropriate by comparing the acquired radiation dose and radiation dose based on the input imaging conditions;
a notification unit that notifies the results determined by the comparison unit; and
an acceptance unit that outputs the input imaging conditions to the image control unit after the input imaging conditions are determined to be appropriate and outputs the determined results to the notification unit after the input imaging conditions are determined to be inappropriate.

3. The X-ray CT system according to claim 1, further comprising:
a measurement unit that comprises:
a scale that measures the weight; and
a body diameter measurement unit that measures the body diameter based on fluoroscopic images of the subject captured by X-raying the subject; and wherein;
the part identification unit identifies the part of the subject being imaged based on the measured weight and the body diameter.

4. The X-ray CT system according to claim 3, wherein;
the part identification unit further comprises:
a table of imaged parts that stores the weight and body diameter of the subject and the part being imaged by mapping them and identifies the part of the subject being imaged by referring to the table of imaged parts.

5. The X-ray CT system according to claim 1, wherein; the notification unit notifies an alarm when the part being imaged is not identified by the part identification unit.

6. The X-ray CT system according to claim 4, wherein; the table of imaged parts treats the weight as an abscissa and the body diameter as an ordinate and furthermore, points on the coordinates that are mapped by the weight and the body diameter are divided into regions representing categories of the part being imaged depending on their positions.

7. The X-ray CT system according to claim 6, wherein; the notification unit notifies an alarm because the part being imaged is not identified by the part identification unit when points on coordinates mapped by the weight and the body diameter are positioned at the boundary between adjacent regions or are positioned in the vicinity of the boundary.

8. The X-ray CT system according to claim 7, wherein; the range of the vicinity of the boundary is composed such that the width is adjusted.

9. The X-ray CT system according to claim 2, further comprising:
a measurement unit that comprises:
a scale that measures the weight; and
a body diameter measurement unit that measures the body diameter based on fluoroscopic images of the subject captured by X-raying the subject; and wherein;
the part identification unit identifies the part of the subject being imaged based on the measured weight and the body diameter.

10. The X-ray CT system according to claim 9, wherein; the part identification unit further comprises:
a table of imaged parts that stores the weight and body diameter of the subject and the part being imaged by mapping them and identifies the part of the subject being imaged by referring to the table of imaged parts.

11. The X-ray CT system according to claim 2, wherein; the notification unit notifies an alarm when the part being imaged is not identified by the part identification unit.

12. The X-ray CT system according to claim 10, wherein; the table of imaged parts treats the weight as an abscissa and the body diameter as an ordinate and furthermore, points on the coordinates that are mapped by the weight and the body diameter are divided into regions representing categories of the part being imaged depending on their positions.

13. The X-ray CT system according to claim 12, wherein; the notification unit notifies an alarm because the part being imaged is not identified by the part identification unit when points on coordinates mapped by the weight and the body diameter are positioned at the boundary between adjacent regions or are positioned in the vicinity of the boundary.

14. The X-ray CT system according to claim 13, wherein; the range of the vicinity of the boundary is composed such that the width is adjusted.

* * * * *